United States Patent [19]

Takeda et al.

[11] 4,233,226
[45] Nov. 11, 1980

[54] NOVEL HEXAHYDROBENZOPYRAN DERIVATIVE AND METHOD OF PREPARING THE SAME

[75] Inventors: Makoto Takeda; Hiroshi Iwane, both of Ami; Takashi Hashimoto, Tokyo, all of Japan

[73] Assignee: Mitsubishi Petrochemical Co., Ltd., Tokyo, Japan

[21] Appl. No.: 69,407

[22] Filed: Aug. 24, 1979

[30] Foreign Application Priority Data

Aug. 24, 1978 [JP] Japan .................................. 53-103322

[51] Int. Cl.³ ........................ C07D 311/74; C11B 9/00
[52] U.S. Cl. ............................. 260/345.2; 252/522 R; 568/444
[58] Field of Search ...................................... 260/345.2

[56] References Cited

U.S. PATENT DOCUMENTS 2,675,393  4/1954  Naves .................................. 260/345.2

Primary Examiner—Nicky Chan
Attorney, Agent, or Firm—Sughrue, Rothwell, Mion, Zinn and Macpeak

[57] ABSTRACT

4a,5,6,7,8,8a-Hexahydro-4,7-dimethyl-4H-1-benzopyran of the formula:

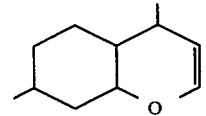

and a method for preparing the same.

1 Claim, No Drawings

NOVEL HEXAHYDROBENZOPYRAN DERIVATIVE AND METHOD OF PREPARING THE SAME

BACKGROUND OF THE INVENTION

1. Field of the Invention

This invention relates to a novel hexahydrobenzopyran derivative which is useful as an odoriferous perfume component and a method of producing such derivative.

SUMMARY OF THE INVENTION

The compound of this invention is 4a,5,6,7,8,8a-hexahydro-4,7-dimethyl-4H-1-benzopyran of the formula (I):

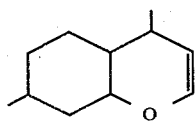

(I)

This compound is aromatic and gives off a distinctive fragrance that is reminiscent of mitcham peppermint. It is prepared by reacting isopulegol with carbon monoxide and hydrogen in the presence of a rhodium catalyst or a cobalt catalyst.

DETAILED DESCRIPTION OF THE INVENTION

Isopulegol used as the starting material in this invention is 2-isopropenyl-5-methylcyclohexanol of the formula (II):

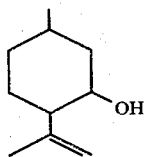

(II)

inclusive of its stereoisomer or isomers due to an asymmetric carbon.

The catalyst used in this invention comprises a rhodium compound or cobalt compound. The rhodium compound is preferred.

Representative examples of the rhodium compound suitable for use as a catalyst in this invention is a complex wherein rhodium is surrounded by a ligand such as a halide, oxide, carboxylate, nitrate, phosphine, amine, olefin, carbon monoxide or hydrogen. Specific examples of the complex are $RhX_3$, $Rh_2O_3$, $[Rh(OCOCH_3)_2]_2$, $Rh(NO_3)_3$, $Rh_6(CO)_{16}$, $[RhX(CO)_2]_2$, $RhX_3(C_5H_5N)_3$, $[RhX(C_8H_{12})]_2$, $Rh(acac)_3$, $RhX(PR_3)_3$, $RhX(CO)(PR_3)_2$, $RhH(CO)(PR_3)_3$ (wherein X is Cl, Br or I; R is an aliphatic group having 1 to 10 carbon atoms or an aromatic group having 6 to 12 carbon atoms). These rhodium catalysts are commercially available. Those which are relatively easily obtained are $RhCl_3$, $Rh_2O_3$, $Rh(NO_3)_3$ and $RhCl(PPH_3)_3$. Preferred for the reaction are $Rh_2O_3$, $Rh_6(CO)_{16}$, $[RhCl(CO)_2]_2$, $RhCl(PPH_3)_3$, $[RhCl(C_8H_{12})]_2$, $RhCl(CO(PPh_3)_2$ and $RhH(CO)(PPH_3)_3$ and of these $RhX(PR_3)_3$, $RhCl(CO)(PR_3)_2$ and $RhH(CO)(PR_3)_3$ are particularly preferred. These rhodium compounds may be used as a homogeneous catalyst or as a heterogeneous catalyst on a porous solid carrier such as activated carbon, alumina or silica.

Representative examples of the cobalt compound that can be used in this invention are Raney cobalt, $Co_2(CO)_8$ and $[PR_3Co(CO)_3]_2$ (wherein R is an aliphatic group having 1 to 10 carbon atoms or an aromatic group having 6 to 12 carbon atoms). Raney Co and $Co_2(CO)_8$ are commercially available.

the rhodium catalyst is used in this invention in an amount in the range of from $1 \times 10^{-1}$ to $1 \times 10^{-6}$ mol, preferably from $1 \times 10^{-2}$ to $1 \times 10^{-5}$ mol, per mol of isopulegol. The cobalt catalyst is used in an amount in the range of from $1 \times 10^{-1}$ to $1 \times 10^{-4}$ mol, preferably from $1 \times 10^{-2}$ to $1 \times 10^{-3}$ mol, per mol of isopulegol.

While either catalyst may be used independently, it is to be understood that for the purposes of inhibiting its decomposition and reducing the reaction pressure, 1 to $10^3$ and preferably 10 to $10^2$ mols of tertiary phosphine may be added to 1 mol of the catalyst.

Suitable tertiary phosphines include compounds of the formula (VI):

(VI)

wherein $R_1$, $R_2$ and $R_3$ are the same or different, and are an aliphatic group having 1 to 10 carbon atoms or an aromatic group having 6 to 12 carbon atoms. Specific examples of tertiary phosphine include trimethylphosphine, triethylphosphine, tripropylphosphine, tributylphosphine, trihexylphosphine, dioctylphenylphosphine and triphenylphosphine.

The reaction for producing the compound of this invention is carried out at a temperature in the range of from about 70° to 200° C., preferably from about 90° to 170° C. Carbon monoxide is mixed with hydrogen at a molar ratio in the range of from about 0.5:1 to 2.0:1 and preferably from about 0.8:1 to 1.2:1. The reaction is carried out at a pressure in the range of from about 1 to 200 kg/cm², preferably from about 30 to 170 kg/cm².

Examples of the solvent which may be used in the reaction include hydrocarbons such as hexane, heptane, benzene, toluene and xylene; ethers such as tetrahydrofuran, dioxane and ethylene glycol dimethyl ether; and chlorinated hydrocarbons such as chlorobenzene and chloroform. Generally, isopulegol is used in these solvents in a concentration of about 10 to 100 vol%, preferably about 20 to 50 vol% based on the volume of the recatants. If desired, the reaction may be carried out in the absence of such solvents.

The reaction product of this invention is purified by isolation from the reaction mixture through distillation or other conventional techniques.

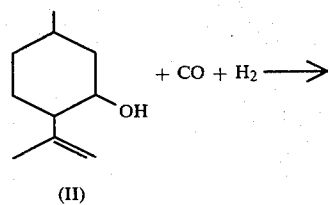

(II)

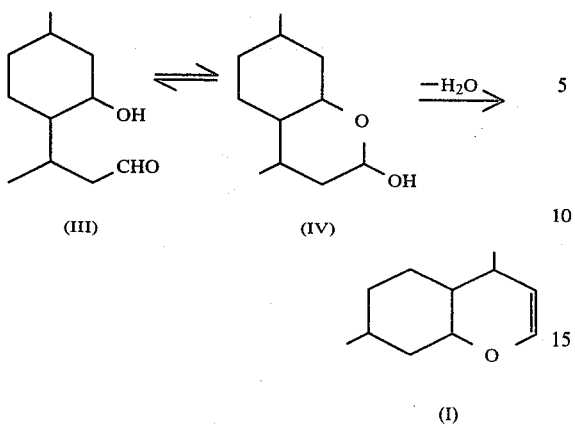

The reaction takes the course identified above wherein hydroformylation of the starting material (II) forms the product (III), 3-(2-hydroxy-4-methylcyclohexyl)-butyraldehyde, which is subjected to rapid intramolecular cyclization to form the product (IV), 4a,5,6,7,8,8a-hexahydro- 4,7-dimethyl-2-chromanol, which is then dehydrated to give the product (I) or the end compound of this invention. The products (III) and (IV) are tautometric isomers for each other.

The compound of this invention is used alone or in combination with natural perfumes or other synthetic perfumes or with conventional additives employed in perfumery. In particular, it may be blended with menthol, peppermint oils or anethole to provide an agreeable and refreshing perfume. The resulting perfume is useful as an ingredient to be incorporated in soaps, detergents, deodorizers, toiletries, cleansers, dentifrices or foodstuffs. A suitable amount for the compound in perfume composition is from about 5 to 100% by weight based on the weight of the perfume composition.

The method of producing the compound of this invention will now be described in greater detail by reference to the following working examples.

EXAMPLE 1

A 100 ml Hastelloy C autoclave was charged with 15 g of isopulegol, 0.09 g of chlorotristriphenylphosphinerhodium, 0.05 g of triphenylphosphine and 30 ml of dioxane. The autoclave was then charged with equal volumes of carbon monoxide and hydrogen which pressurized the autoclave to 100 kg/cm². The reaction was carried out at a temperature of 140° C. and at a pressure of 90 to 120 kg/cm² for a period of 5 hours. After cooling, the pressure was reduced to atmospheric, and the reaction mixture was recovered from the autoclave and distilled for purification which yielded 15.6 g of 4a,5,6,7,8,8a-hexahydro-4,7-dimethyl-4H-1-benzopyran having a boiling point of from 64° to 66° C. at 0.5 mmHg. The IR and NMR spectra of the product had the following absorption characteristics:

IR Spectrum (liquid film): 3060, 1645, 1240 cm$^{-1}$
NMR Spectrum (solvent: CDCl$_3$, δ ppm):
0.7–2.2 (15H, m), 3.8 (1H, m), 4.80 (1H, dd), 6.35 (1H, dd) (m = multiplet, dd = double doublet)

The product had a distinctive odor suggestive of mitcham peppermint.

EXAMPLE 2

A 100 ml Hastelloy C autoclave was charged with 10 g of isopulegol, 0.4 g of dicobalt octacarbonyl and 25 ml of toluene. The autoclave was then charged with equal volumes of carbon monoxide and hydrogen which pressurized the autoclave to 150 kg/cm². The reaction was carried out at a temperature of 110° C. and at a pressure of 160 to 140 kg/cm² for a period of 6.5 hours. After cooling, the pressure was reduced to atmospheric, and the reaction mixture was recovered from the autoclave and distilled for purification which yielded 4a,5,6,7,8,8a-hexahydro-4,7-dimethyl-4H-1-bennzopyran having a boiling point of from 84° to 90° C. at 2.5 mmHg.

While the invention has been described in detail and with reference to specific embodiments thereof, it will be apparent to one skilled in the art that various changes and modifications can be made therein without departing from the spirit and scope thereof.

What is claimed is:
1. 4a,5,6,7,8,8a-hexahydro-4,7-dimethyl-4H-1-benzopyran of the formula:

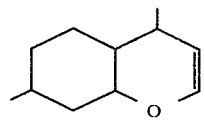

* * * * *